United States Patent [19]
Roth

[11] Patent Number: 5,209,725
[45] Date of Patent: May 11, 1993

[54] PROSTATIC URETHRA DILATATION CATHETER SYSTEM AND METHOD

[76] Inventor: Robert A. Roth, 29 Hyslop Rd., Brookline, Mass. 02146

[21] Appl. No.: 683,725

[22] Filed: Apr. 11, 1991

[51] Int. Cl.$^5$ ............................................. A61M 31/00
[52] U.S. Cl. ........................................ 604/53; 604/96; 606/191; 128/7
[58] Field of Search .................. 606/108, 191–192, 606/194, 198, 13–17, 7; 604/53, 96–104; 128/4.7

[56] References Cited

U.S. PATENT DOCUMENTS

| | | | |
|---|---|---|---|
| 2,799,273 | 7/1957 | Oddo | 604/101 |
| 2,849,002 | 8/1958 | Oddo | 604/101 X |
| 4,248,214 | 2/1981 | Hannah et al. | 128/7 |
| 4,445,892 | 5/1982 | Hussein et al. | 604/101 |
| 4,470,407 | 9/1984 | Hussein | |
| 4,660,560 | 4/1987 | Barken | |
| 4,672,963 | 6/1987 | Klein | |
| 4,738,659 | 4/1988 | Sleiman | 604/96 |
| 4,762,128 | 8/1988 | Rosenbluth | |
| 4,772,093 | 9/1988 | Abele et al. | 350/96.25 |
| 4,932,958 | 6/1990 | Reddy et al. | 606/192 |
| 4,951,677 | 8/1990 | Crowley et al. | 128/662.06 |
| 5,002,558 | 3/1991 | Klein et al. | 606/192 |
| 5,007,897 | 4/1991 | Kalb et al. | 604/43 |
| 5,007,898 | 4/1991 | Rosenbluth et al. | |
| 5,100,424 | 3/1992 | Jang et al. | 606/159 |
| 5,116,317 | 5/1992 | Carson, Jr. et al. | 604/96 |

OTHER PUBLICATIONS

PCT Published Application No: WO 90/13333; Publication Date: Nov. 15, 1990; Applicant: Intra-Sonix, Inc.
Harvard Medical Health Letter, Sep. 1988, vol. 13, No. 11, pp. 1–4.
Castaneda, Flavio et al., "Prostatic Urethra: Experimental Dilation in Dogs", Radiology, Jun. 1987, pp. 645–648.
Castaneda, Flavio et al., "Benign Prostatic Hypertrophy: Retrograde Transurethra Dilation of the Prostatic Urethra in Humans", *Radiology*, Jun. 1987 pp. 649–653.
Smith, Jr., Joseph A. et al: "Laser Photoradiation in Urologic Surgery", The Journal of Urology, vol. 13, Apr. 1984, pp. 631–635.
*Astra Urologue*, Astra Pharmaceutical Products, Inc., Westborough, Mass., May 1990, pp. 1–8.
Dowd, Joseph B. et al, Ed., "Balloon Dilatation of the Prostate, Concept and Technique", Microvasive Education Center, Boston Scientific Corp., Boston, Mass.
Klein, Lester A. "Transcystoscopic Balloon Dilatation of the Prostate", published at the AUA Meeting in New Orleans, La., May 12–May 17, 1990.
Dowd, Joseph B. et al., "Balloon Dilatation of the Prostate", published at the A.U.A. Meeting in New Orleans, La., May 12–17, 1990.

*Primary Examiner*—C. Fred Rosenbaum
*Assistant Examiner*—C. Maglione
*Attorney, Agent, or Firm*—Schiller & Kusmer

[57] ABSTRACT

An improved instrument for and method of performing a transurethral balloon dilatation procedure of the prostate is disclosed. The instrument includes a hollow catheter comprising a shaft having at least its distal end portion made of an optically transparent material, and a substantially non-compliant, inflatable, optically transparent balloon attached at the distal end portion of the catheter and sized to dilate the prostatic urethra so as to post-operatively open that passageway. The catheter is provided with at least one suitable marking so as to indicate at least the location where the proximal end of the balloon is attached to the catheter body. Preferably, the marking is provided at a location that when positioned at visible landmarks, preferably the external sphinter, or the apex or verumontanum of the prostate, the balloon will be correctly positioned relative to the external sphincter muscle at the apex of the prostate. The shaft of the catheter is dimension so that a standard viewing instrument such as an optic of a commercially available endoscope can be moved through the shaft and utilized to locate the balloon relative to the relevant anatomical landmarks of the prostate before and during the dilatation procedure.

12 Claims, 3 Drawing Sheets

PROSTATIC URETHRA DILATATION CATHETER SYSTEM AND METHOD

The present invention relates generally to instruments for relieving stenosis of the prostatic urethra, and more particularly to balloon dilatation of the prostatic urethra.

BACKGROUND OF THE INVENTION

As is generally known the prostate is located at the base of the bladder, where it surrounds a portion of the urethra, the tube connecting the bladder and the outside world. The function of the prostate is to produce a fluid which becomes a part of the ejaculated semen (which is carried through the urethra). As men grow older, the tissue of the prostate often begins to enlarge, a condition known as hyperplasia. As the bulk of the prostate enlarges, the gland begins to constrict the portion of the urethra passing through the prostate and thus prevent the normal flow of urine, a condition known as benign prostatic hypertrophy or hyperplasia (BPH). As BPH develops, one or more constricted or stenotic regions within the prostatic urethra can from time to time obstruct the flow of urine; so the signs of BPH are difficulty starting urination, dribbling following urination, reduced force of the stream of urine, a tendency to urinate frequently in small amounts as well as pain and discomfort. As a result an increase in urinary tract infections can occur. The symptoms are common, 75-80% of men over the age of fifty are affected. See, for example, the *Harvard Medical Health Letter;* September 1988; Volume 13; Number 11; pages 1-4 and Castaneda, Flavio et al.; "Prostatic Urethra: Experimental Dilation in Dogs"; *Radiology;* June, 1987; pp. 645-648. In fact recent statistics apparently reveal that a 50 year old man has a 20-25% chance of undergoing treatment for this condition during his lifetime. See Casteneda et al., suora; and PCT International Published Application 90/13333.

When the obstructive symptoms of BPH become bothersome, the constricted portions of the urethra are usually reopened surgically. Current accepted treatment for BPH involves either open or transurethral surgery, which is costly and is associated with an acceptable but undesirable degree of mortality (estimated from 1.3% to 3.2% see Castaneda, Flavio et al.; "Benign Prostatic Hypertrophy: Retrograde Transurethral Dilation of the Prostatic Urethra in Humans" *Radiology;* June, 1987, pp. 649-653), and with a significant degree of morbidity, especially with less fit patients.

The most common surgical procedure for BPH, as an alternative to open surgery, is a transurethral resection of the prostate, or TURP. The transurethral resection involves inserting a resectoscope through the urethra. A spring wire, adapted to carry an electric current, is inserted through the resectoscope for use in removing tissue. The wire carries one current for cutting away "chips" of tissue with the resectoscope and another current for cauterizing the remaining tissue to minimize bleeding. As much as two cubic inches of tissue are removed in this way.

The TURP surgical technique is not trivial nor inexpensive, though the actual procedure can ordinarily be done within one hour. The procedure carries similar risks as many of those associated with other general surgical procedures. In addition, intraoperative irrigation fluids are required to flush blood from the prostatic urethra while tissue is being removed creating a danger that the flushing fluid will enter the blood circulatory system through iatrogenic openings into veins causing fluid overload and possible death, a result known as "post-TURP" syndrome. Other surgical hazards include stricture formation at the urethra or bladder neck, post-manipulation pain or bladder spasm, urinary tract infections, and reactive urethral swelling which can cause urinary obstruction and epididymitis. Other complications include retrograde ejaculation and delayed recurrent obstruction of the bladder neck area. Further, the post-operative care following a TURP procedure requires a prolonged hospital stay, creating substantial costs for medical care. The appropriate DRG (Diagnostically Related Group), currently designated by Medicare, for the TURP procedure presently entails an average length of hospital stay of 5.8 days. Accordingly, current pressures exist to reduce allowable Medicare fees for the TURP procedure and the impact of such reduced fees on urological patient care and the American urologist. In addition, some men have reported sexual dysfunction following a resection. Certain men have also become incontinent as a result of the surgery because of inadvertent damage done to the external sphincter muscles positioned at the apex of the prostate for controlling urine flow. The surgery usually results in moderate discomfort with some post-operative bleeding being usual.

As a result of the trauma that many men experience from TURP and the relatively long in-patient care required for post operative recovery, alternative techniques of treating BPH are being investigated. For example, recent attention has been given to laser surgery to relieve obstruction. See, for example, U.S. Pat. No. 4,672,963 issued to Dr. Israel Barken, and Smith, Jr., Joseph A. et al.; "Laser Photoradiation in Urologic Surgery"; *The Journal of Urology;* Vol. 31, April, 1984, pp. 631-635, cited therein. Also see PCT Published Application No. WO 90/13333.

Other alternatives of open prostatectomy and the TURP procedure and open prostatectomy include long-term hormone treatments with, for example, alpha-adrenergic blockers, enzymes (e.g., 5 alpha-reductase inhibitors), or antiandrogens, in order to prevent or reverse prostate enlargement. However, there have been some uncertainties about the role played by hormones in creating BPH. Transurethral incision of the prostate (TUIP) is another approach, although its risks are not much different from the TURP procedure. A device for transrectally applying thermal therapy to the transitional zone of the prostatic urethra with microwave energy is being marketed by the Armonite, Inc. of NY. The long term results of such therapy are currently inconclusive.

Finally, balloon dilatation of the prostatic urethra has received a great deal of recent attention with the development of dilatation balloon technology. In this latter approach a catheter having an inflatable non-compliant balloon positioned at the distal end of the catheter is transurethrally inserted into the prostatic urethra. The balloon is then inflated so that the expanding balloon dilates the urethra and is held in its inflated state for a limited period of time, e.g., between ten and sixty minutes. See, for example, Castaneda, et al. "Prostatic Urethra: Experimental Dilation in Dogs"; *Radiology;* June, 1987, pp. 645-648; and Castaneda, et al.; "Benign Prostatic Hypertrophy: Retrograde Transurethral Dilation of the Prostatic Urethra in Humans"; *Radiology;* June, 1987; pp 649-653. See also U.S. Pat. No. 4,660,560 issued to Klein; Astra Urologue, Astra Pharmaceutical Products, Inc. Westborough, MA, May 1990, pp 1-8; and Dowd, Joseph B. et al., Ed., "Balloon Dilatation of the Prostate, Concept and Technique" Microvasive Education Center, Boston Scientific Corporation, Boston, MA. During the balloon dilatation procedure the tissue of the prostatic urethra must be expanded beyond its normal elastic limit, otherwise the urethra will not remain dilated for very long since the tissue will rebound to a certain extent. Accordingly, the balloon is sized to expand, for example, to a 25 mm to 30 mm diameter so as to cause the tissue within the averaged sized prostate to stretch to the point of actually tearing or cracking so that when the tissue heals, permanent fissures will remain so that urethra will remain dilated. Such a procedure will not always insure long term effects of relieving the stenosis and constriction of the urethral walls due to the nature of the resilient muscle tissues and large bulk of the hypertrophied prostate which has a tendency to rebound after temporary compression. Accordingly, as described in U.S. Pat. No. 4,762,128 issued to Rosenbluth, the latter proposes to insert a stent in the prostatic urethra after being dilated by the balloon and remove the stent at a later time, although the stents are difficult to remove once they have been inserted and create a tendency for irritation and encrustation.

While all of these procedures have advantages, at the present time sufficient data do not exist that suggest one "best" alternative. However, of the alternative approaches, balloon dilatation seems to be one of the safer, more proven approaches for providing at least short term relief for urinary outflow obstruction.

Historically, as early as mid-nineteenth century, a number of instruments were specifically developed to dilate the prostatic urethra and bladder neck. The most widely used was a metal dilator designed by Mercier in 1850. In 1910, tranvesical digital dilatation of the bladder neck and prostate was described. This technique was performed through a small suprapubic cystotomy and was associated with lower morbidity and mortality than the open prostatectomy. In 1956, Deisting and Frank developed a metal dilator that was a modification of Mercier's design. Using a retrograde transurethral approach, the metal dilator was positioned across the prostate. Correct position was confirmed by rectal digital palpation. When opened, the dilator would disrupt the anterior and posterior prostatic commisures. The use of dilatation techniques as an alternative to open prostatectomy began to wane as the use of the TURP began to increase. However, recent studies questioning the safety and efficacy of TURP and the development of improved balloon technology for such purposes have rekindled interest in the transurethral balloon dilatation procedure.

When performing a balloon dilatation procedure of the prostate, it is most important that steps are taken to insure that the inflatable balloon is properly positioned within the prostatic urethra during the procedure. In fact of all the variables of balloon design and operative technique, proper placement of the balloon relative to the apex of the prostate is most critical, both at the beginning and during the entire inflation period. In accordance with at least one approach, the length of the balloon is chosen based upon the premeasured size of the prostatic urethra so that the external urethra and bladder neck are not damaged while the balloon is inflated. If the balloon is too large or is incorrectly positioned within the prostatic urethra so that a portion of the balloon inflates in the external sphincter at the apex of the prostate, for example, the sphincter and apex may be damaged in such a manner as to cause incontinence. Accordingly, care must be taken to measure the location and size of the prostate before performing this dilatation procedure. One of the earliest attempts to visualize placement of the balloon was accomplished by placing radioopaque markings on the catheter so that the markings could be observed fluoroscopically as the balloon catheter was inserted into the prostate under X-ray control. Although the early results were encouraging, the fluoroscopic approach requires the cooperation of a radiologist, creating unnecessary scheduling and cost problems, and alone was not always sufficiently precise in providing localization of the dilatation balloon within the prostatic urethra.

Another instrument for performing prostatic balloon dilatation is the Dowd TM Prostatic Balloon Dilatation Catheter manufactured by Microvasive, an affiliate of Boston Scientific Corporation of Boston, MS. The latter in Dowd, Joseph B., et al.; "Balloon Dilatation of the Prostate", published at the A.U.A. meeting in New Orleans, LA, May 12-17, 1990, includes an inflatable, substantially non-compliant balloon (typically made of polyethylene terephthalate), positioned on the distal end of a catheter. The catheter is adapted to be transurethrally inserted through the urethra so that the balloon is located in the portion of the urethra extending through the prostate. The balloon is then inflated, typically to a pressure of about four atmospheres, so that the expanding balloon dilates the urethra and is held in its inflated state for a limited period of time, e.g., about ten minutes. The balloon is sized to expand to a 30 mm diameter (90 F) giving fairly good results, better than a smaller 75 F balloon.

The Dowd TM Dilation Ctheter utilizes a single balloon having an effective dilating length of 5 cm to ensure adequate dilation of both the prostatic capsule along the full length of the prostatic urethra as well as the bladder neck. The proper balloon position however is accomplished by transrectal digital palpation. Specifically, a 19 F positioning nodule is provided on the catheter proximal to the balloon so as to permit precise placement using transrectal digital control. This assumes, however, that by transrectally sensing the nodule at a certain position, the balloon will be properly positioned distal to the apex of the prostate. However, the anatomy of prostate can not be precisely felt transrectally, i.e., the location of the apex of the prostate and external sphincter may not be where the physician believes it to be, and may in fact move with the insertion of the balloon catheter and even deform with balloon dilatation.

Another approach utilizes a trans-cystoscopic technique, described in the Astra Urologue publication, supra, and in U.S. Pat. No. 5,007,898 and Klein, Lester A., "Transcystoscopic Balloon Dilatation of the Prostate", published at the A.U.A. meeting in New Orleans, LA, May 12-17, 1990. The approach described in the later apper, as well as U.S. Pat. No. 4,660,560 involves the insertion of a standard cystoscope into the prostatic urethra. The cystoscope includes a metal sheath and an optic. The latter is an instrument for optically viewing the prostatic urethra intralumenally and is adapted to slide into the sheath and lock into but a single position at the end of the sheath. The cystoscope is used to evaluate the prostate and surrounding structures. By moving the entire instrument along the urethra, the bladder is usually inspected for incidental pathology and the external sphincter is clearly located so as to avoid damaging the latter. A separate, specially designed measuring catheter, with calibration markings provided at predetermined axial intervals (e.g. 1 cm spacings) with an inflatable balloon located at its end, is next inserted through the cystoscope, and secured beyond the end of the cystoscope at the bladder neck with the inflatable balloon. The distance between the bladder neck and the external sphincter is determined with the cystoscope, which is moved along the urethral passageway relative to and external of the calibration catheter, by viewing the calibration markings on the latter device. A plurality of catheters, provided with various length-sized balloons, are made available so that based on the measurement obtained, the proper balloon length can then be chosen. The chosen balloon catheter is then inserted into the prostatic urethra via the cystoscope. At the end of the balloon catheter is a Foley balloon that is inflated beyond the distal end of the cystoscope, within the bladder before the inflation of the dilatation balloon so as to anchor the dilatation balloon in its proper position within the prostatic urethra. A localization band on the balloon catheter is provided a predetermined distance, e.g., 0.5 cm, from the dilatation balloon, distal to the external sphincter and assists in the proper positioning of the dilatation balloon relative to the apex of the prostate. This band is then visualized just distal to the external sphincter within the prostatic urethra (with the external sphincter being visualized as well) through the specially designed cystoscope which is moved within the urethra to a position where the band is in view just distal from the distal end of the cystoscope and external of the balloon catheter. In this technique the bladder neck is not dilated.

During the dilatation process (i.e., the inflation of the balloon), the view of the dilatation balloon and prostate is obscured, so that the urologist relies on the localization band to ensure that the balloon catheter is properly positioned before the balloon is inflated. The dilatation catheter contains an irrigation channel allowing visualization and irrigation. Once the positioning of the balloon is confirmed, the balloon is inflated to its inflated dimensions at the inflated pressure (e.g., 3 atmosphere) for the predetermined time (e.g., 10 minutes) for providing the dilatation of the prostatic urethra. Since the balloon has a tendency to move toward the bladder as it is inflated, the localization band (and thus indirectly the balloon) is monitored by the cystoscope to insure that the balloon does not move. Once inflated, if the dilating balloon is correctly positioned it does not usually migrate since the bladder neck is trapped between the two inflated balloon. After the time period of balloon inflation passes, the balloons are deflated and withdrawn through the cystoscope. Withdrawing the balloon through the cystoscope protects the urethra from being traumatized by the balloon.

While the above cystoscopic measurements work reasonably well in providing the proper size of and position for the balloon, the use of multiple instruments makes the procedure more cumbersome and time consuming and difficult for the patient. Continual monitoring of the localization band with the cystoscope creates a less accurate positioning technique due to the fact that it is indirectly related to the actual positions of the landmarks of the prostate and ignores any possible movement of the cystoscope itself.

OBJECTS AND SUMMARY OF THE INVENTION

Accordingly, it is an object of the present invention to overcome or substantially reduce the above-noted problems of the prior art.

Another object of the present invention is to provide an improved balloon dilatation catheter for relieving urinary outflow obstruction.

And another object of the present invention is to provide an improved balloon dilatation catheter for intraluminal visualizing the landmarks of the prostatic urethra while inflating the dilatation balloon so as to provide easy localization of the balloon and allowing continuous monitoring of the position of the balloon during the entire dilatation procedure.

Yet another object of the present invention is to provide an easy way to localize a prostatic dilatation balloon and monitor the position before and during the procedure without the need for digital palpation, or the use of X-rays or additional instruments such as a calibration catheter.

Still another object of the present invention is to provide a prostatic balloon of a universal size and useful in balloon dilatation of prostates of all sizes so as to eliminate the need and expense of having to provide multiple balloon sizes.

And yet another object of the present invention is to reduce the costs and of the above described prostate dilatation procedures by using a commercially-available optic to view the anatomical landmarks before and during the procedure.

These and other objects of the present invention are provided by an improved instrument for and method of performing a transurethral balloon dilatation procedure of the prostate. The instrument includes a hollow catheter comprising a shaft having at least its distal end portion made of an optically transparent material, and a substantially non-compliant, inflatable, optically transparent balloon attached at the distal end portion of the catheter and sized to dilate the prostatic urethra so as to post-operatively open that passageway. The catheter is provided with at least one suitable marking so as to indicate at least the location where the proximal end of the balloon is attached to the catheter body. Preferably, the marking is provided at a location that when positioned at a recognizable anatomical landmark, preferably either the verumontanum or apex of the prostate, the balloon will be correctly positioned relative to the external sphincter muscle at the apex of the prostate. The shaft of the catheter is dimension so that a standard viewing instrument such as an optic of any commercially available endoscope can be moved through the shaft and utilized to locate the balloon relative to the relevant anatomical landmarks of the prostate before and during the dilatation procedure. These observations are made by viewing anatomical landmarks directly through the walls of the optically clear sheath and balloon.

Other objects of the invention will in part be obvious and will in part appear hereinafter. The invention accordingly comprises the processes involving the several steps and the relation and order of one or more of such steps with respect to each of the others, and the apparatus possessing the construction, combination of elements, and arrangement of parts which are exemplified in the following detailed disclosure, and the scope of the application of which will be indicated in the claims.

BRIEF DESCRIPTION OF THE DRAWINGS

For a fuller understanding of the nature and objects of the present invention, reference should be had to the following detailed description taken in connection with the accompanying drawings wherein.

DETAILED DESCRIPTION OF THE DRAWINGS

In the drawings the same numerals are used to designate the same or similar parts.

Figure 1:
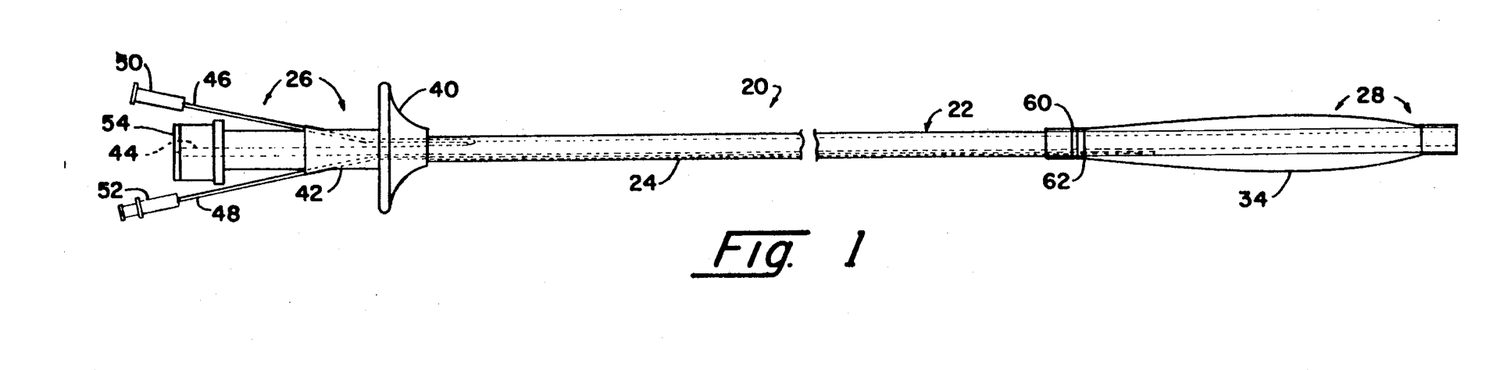
FIG. 1 is a side view of the preferred embodiment of the dilatation balloon catheter designed in accordance with the present invention.
Figures 2, 3, 4:
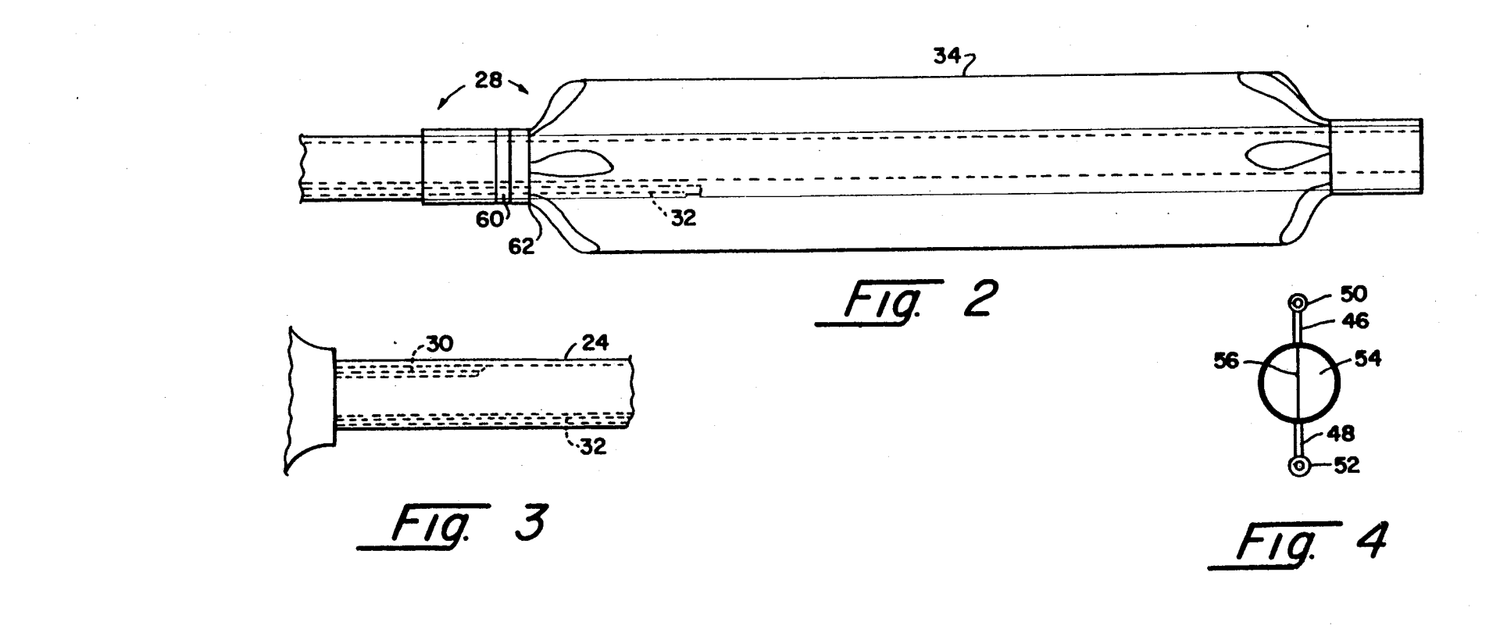
FIG. 2 is a side view, partially cut away of the distal end of the FIG. 1 catheter.
FIG. 3 is a side view, partially cut away, showing details where the main portion of the catheter is formed with the proximal portion of the FIG. 1 catheter.
FIG. 4 is a view of the proximal end of the FIG. 1 catheter.

Referring to FIGS. 1–4, the preferred catheter 20 of the present invention includes a hollow shaft 22 which may be extruded from an appropriate polymer, such as polyvinyl chloride or polyethylene. The material utilized must be such that at least the distal portion of the shaft is optically clear so that anatomical landmarks can be viewed intraluminal through the wall of the shaft. The shaft 22 includes a main portion 24 disposed between the proximal and distal end portions 26 and 28, respectively. The cross-sectional diameter and wall thickness of the shaft is substantially constant along the entire axial length of the shaft. The actual dimensions are somewhat variable, with a 20 cm length, 5 mm diameter outside cross-sectional diameter, and a wall thickness on the order of 1 mm being typical, although the shaft is dimensioned so that a standard sized optic of a commercially available cystoscope is (a) longer than the shaft such that the attending physician can move the optic all the way into the shaft with a portion of the optic still extending from the shaft, and (b) is of an internal cross-section so that the optic can easily slide axially through the shaft with some radial movement being permissible if not desirable. The shaft 22 is relatively stiff with some flexibility so that the catheter, with the aid of a suitable lubricant, can be easily guided through the urethra without the shaft kinking or buckling. A pair of relatively small lumens 30 and 32, on the order of 0.5 mm in cross-section, are provided in the wall of the shaft, one lumen 30 extending from the outside of the proximal portion 26 of the shaft to the interior of the main portion 24, and the other lumen 32 extending from the outside of the proximal portion to the outside of the distal portion 28 (as seen in FIGS. 1 and 2). The lumen 32 communicates with a dilatation balloon 34 secured to the distal portion 28 and described hereinafter. The proximal portion 26 of the shaft 22 is provided with a finger grip 40, bifurcated fitting 42 and the fitting 44 for gripping the optic 70 (described hereinafter), all secured adjacent one another to the proximal end of the shaft 22.

Finger grip 40 is preferably in the form of a contoured disk so that the attending physician can more easily push and pull the catheter to and from its operative position, as described in greater detail hereinafter.

A bifurcated fitting 42 is secured to the outside of the shaft adjacent the seal fitting 44 the proximal portion of the shaft. The bifurcated fitting supports two small tubes 46 and 48, respectively connected to the two lumens 30 and 32. Tube 46 is used for transmitting irrigation fluids through the shaft 22 into the anatomical region of interest (including the bladder). The shaft provides a return path for the irrigation fluids. Tube 48 is used for transmitting a non-compressible fluid, such as a saline solution, for inflating the dilatation balloon 34. The tubes are provided with luer connectors 50 and 52, for connecting the catheter to adaptors, syringes, inflation devices and the like, as will be more apparent hereinafter. Stopcocks (not shown) can be attached to each luer connector for opening and closing the tube as desired.

Fitting 44 is provided with a flexible gripping element 54 best shown in FIG. 4. The fitting 44 is a flat piece of flexible material, such as neoprene rubber or other elastomer, cut so as to form center slit 56 so that when the optic 70 is inserted through the slit 56 as described hereinafter, the fitting 44 will remain secure against the body of the optic so as to provide fluidic seal and to stabilize the instrument to facilitate viewing by retarding axial and radial movement of the optic when viewing through the optic. It should be evident that other sealing means can be used alternatively to the flat piece of flexible material, such as a compressible 0-ring.

The dilatation balloon 34 is attached to the distal end portion 28 of the shaft 22 so that it is sealed around the shaft at its two ends. The balloon is attached to the shaft in a manner well known in the art. The balloon is made of a suitable, optically clear, substantially non-compliant, yet inflatable material, such as polyethylene terephthalate (PET), or other copolymer, polyester, or copolyester material commonly used to form dilatation balloons. The thickness of the balloon is preferably about 0.1 mm, although the thickness can vary. The only limitation on the thickness and tensile strength of the balloon is that it withstand the inflated pressure of the non-compressible fluid when fully inflated. This pressure is typically about 2 to 4 atmospheres of pressure, although the pressure level can vary. The balloon is sized so that when fully inflated it is about 30 mm in diameter (90 F) along substantially its entire length. The axial length of the balloon is sufficiently long so that one balloon can be used with all prostates. For example, a balloon of 5–6 cm length is suitable. In accordance with the present invention a marker 60 is provided at an axial position at a predetermined position relative to the end 62 of the inflatable proximal portion of the balloon where it is attached to the shaft (as seen in FIGS. 1 and 2) to provide a visible marking to enable localization of the catheter before and during the dilatation procedure.

Specifically, the marker is provided at a shaft position so that when it is located at the position of the verumontanum (a small bump projecting into the prostatic urethra which can be visibly seen intralumenally by the optic 70) the inflatable proximal end 62 of the balloon will be safely positioned relative to the external sphincter at the apex of the prostate while providing dilation in all three lobes of the prostate. Since the external sphincter and the apex of the prostate are not dilated by the portion of the balloon in that position, the verumontanum and external sphinter each provides a good landmark because it can still be identified to the trained eye, through the optic even after balloon 34 is inflated.

In accordance with the present invention an optic 70 of a standard cystoscope is used to localize the catheter. An example of an optic is one manufactured by Karl Storz Hopkins Lens, #27015 30° lens having a 4 mm outer diameter, provided with a commercially available cystoscope manufactured by that company. As is well known, the typical optic is a device having a long shaft with an ocular lens at its proximate end, reflecting means, such as a prism, at its distal end for bending the optical axis and forming a focussed view transversely to the shaft at the distal end. A fiber optic light bundle is provided between the ocular lens and the prism, while an objective lens is provided at its distal end for forming a focal image which is viewed by the ocular lens.

Figure 5:
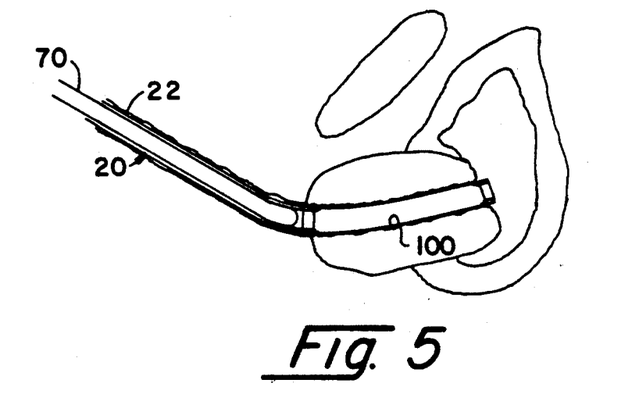
FIG. 5 shows a standard optic being inserted through the FIG. 1 catheter, so that the instrument can be properly inserted, and anatomical landmarks can be easily and directly observed prior to and during the inflation of the dilatation balloon so as to insure proper localization of the balloon during the dilatation process.
Figure 6:
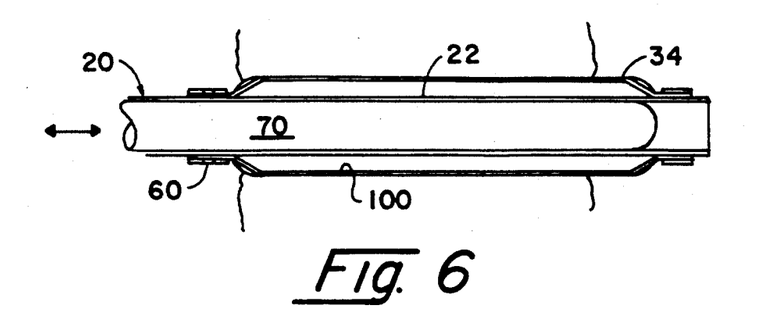
FIG. 6 shows the optic positioned within the distal end of the FIG. 1 catheter prior to inflation of the balloon.

In accordance with the preferred method of using the present invention, the patient is properly prepared and provided with a suitable anesthesia. Next, as shown in FIG. 5 and 6 the shaft with optic in place, is guided through the urethra by direct visualization through the optic so that the balloon end of the shaft protrudes into the bladder. The optic/shaft is then drawn back into the prostatic urethra so that the end of the shaft allows a clear view of the apex/verumontanum area of the prostatic urethra. Keeping the chosen landmark in view through the optic and the transparent wall of the shaft, the shaft is pushed forward so that the balloon is properly positioned in the prostatic urethra and the aligning mark is now located over the landmark. Alternatively, after the shaft is in the bladder neck area, the optic can be pulled back into the shaft until the chosen landmark is identified and then keeping the landmark in view through the optic, the shaft is pulled back so that the aligning mark is placed over this land mark.

Figure 7:
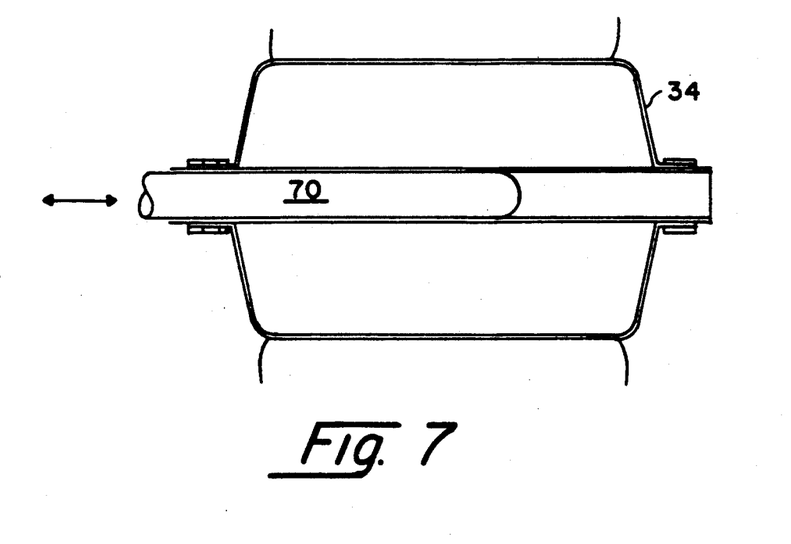
FIG. 7 shows the optic used so as to insure that the inflated balloon does not slip during the dilatation process.

As shown in FIGS. 5 and 6, once the anatomy is determined (as suggested by FIG. 6), and the mark 60 is correctly positioned relative to the chosen anatomical landmark the balloon 28 will be correctly positioned relative to the external sphincter muscle positioned at the proximal apex of the prostate. The attending physician can freely move the optic above the shaft to observe the entire position of the deflated balloon. Once the correct position of the balloon can be assured, the balloon can be inflated as illustrated in FIG. 7. This is accomplished by introducing the inflating fluid through the tube 46 and lumen 30 into the balloon 28, while the physician holds the finger grip 40. As the balloon is inflated, the counter compressive forces exerted by the prostate create a strong tendency for the balloon to be extruded into the bladder. However, as seen in FIG. 7, because the catheter and balloon are optically clear, the optic can be used by the physician to monitor the exact position of the balloon both during its inflation, and while it remains inflated, by observing the position of the marker 60 relative to the chosen anatomical landmark.

Figure 8:
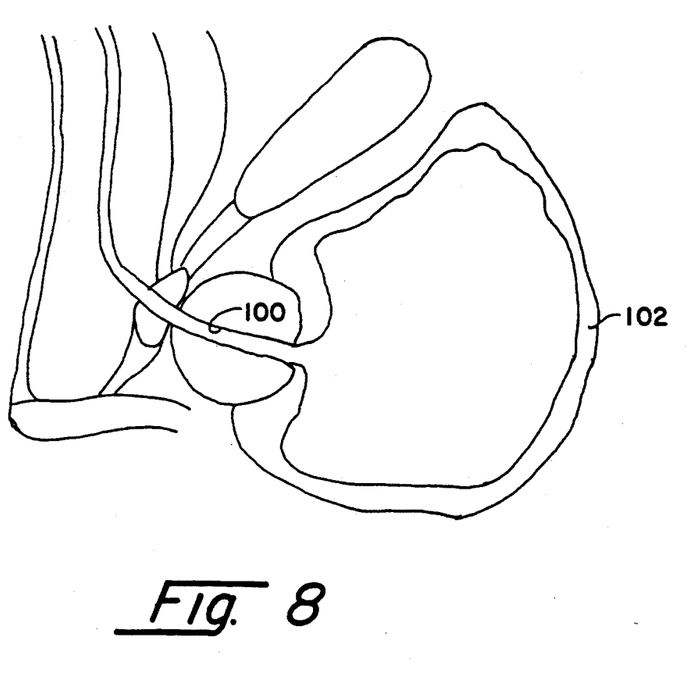
FIG. 8 is an anatomical drawing showing the idealized state of the prostatic urethra following the dilatation procedure.

The balloon remains in the inflated state for the prescribed period of time determined by the physician (typically between ten and sixty minutes). After the requisite period the tissue of the prostatic urethra is sufficiently stretched so that when the balloon is deflated and the optic and catheter withdrawn, the prostatic urethra will remain open, as suggested by FIG. 8.

The system formed by the catheter 20 and optic 70 provides an improved prostatic urethra dilatation system since it provides a precise way to localize the dilatation balloon and monitor the position before and during the dilatation procedure without the need for digital palpation, or the use of X-rays or additional instruments such as the calibration catheter described above. The balloon 28 is a single size so as to eliminate the need and expense of having to provided multiple balloon sizes. The system is of a reduced cost since a commercially available optic can be used to view the anatomical landmarks before and during the procedure.

It should be appreciated that while the present invention has been described as useful in balloon dilatation of the prostatic urethra, it has other applications where a balloon catheter must be precisely positioned relative to certain anatomical landmarks, such as angio-plasty balloon catheters, etc.

Since certain changes may be made in the above apparatus and process without departing from the scope of the invention herein involved, it is intended that all matter contained in the above description or shown in the accompanying drawing shall be interpreted in an illustrative and not in a limiting sense.

What is claimed is:

1. A method of intra-operatively dilating the prostatic urethra with an instrument including a hollow ctheter including a shaft having at least its distal end portion made of an optically transparent material, a substantially non-compliant, inflatable optically transparent balloon attached at the distal end portion of the catheter and sized to dilate the prostatic urethra so as to post-operatively open the latter, and at least one suitable visible marking disposed on the distal end portion of said catheter at a location which when viewed intralumenally transversely through said shaft relative to a predetermined anatomical landmark properly position said balloon relative to the prostatic urethra prior to and during the dilation of the prostatic urethra with said balloon; ad optical viewing means, adapted to slide in said shaft, for visibly viewing the interior of the prostatic urethra in a transverse direction through the distal end portion, said method comprising the steps of:

inserting said catheter so that said balloon is positioned in the proximity of said prostatic urethra;

moving said optical viewing means through said shaft to a position so as to view said anatomical landmark in a transverse direction through said distal end portion;

moving said catheter to the extent necessary so as to position sad marking at said anatomical landmark;

inflating said balloon for the time period necessary to intra-operatively dilate said prostatic urethra while monitoring the position of said marking relative to said anatomical landmark with said optical viewing means; and deflating said balloon and withdrawing said catheter and viewing means from the urethra.

2. The method according to claim 1, wherein said landmark is the verumontanum of the prostate.

3. The method according to claim 1, wherein said landmark is the external sphinter of the prostate.

4. The method according to claim 1, wherein said landmark is the apex of the prostate.

5. The method according to claim 1, wherein said optical viewing mean is an optic of a cystoscope.

6. An improved instrument for performing a transurethral balloon dilatation procedure of the prostate, said instrument comprising, in combination:

a hollow catheter including (a) a shaft having at least its distal end portion made of an optically transparent material, (b) a substantially non-compliant, inflatable optically transparent balloon attached to the distal end portion of the shaft and sized to dilate the prostatic urethra so as to post-operatively open the latter, and (c) at least one suitable visible marking (i) disposed on said catheter and (ii) positioned relative to said balloon such that the marking can be visualized in a transverse direction from within said distal end portion relative to a predetermined anatomical landmark so as to properly position said balloon relative to the prostatic urethra prior to and during the dilation of the prostatic urethra with said ballon; and optical viewing means, slidable within said catheter, for visibly viewing said marking intraluminally from within said catheter transversely through said distal end portion of said shaft relative to said predetermined anatomical landmark prior to and during the dilation of the prostatic urethra with said balloon so as to insure the proper positioning of the balloon relative to the anatomical landmark prior to and during said dilation.

7. An instrument according to claim 6, wherein said visible marking is provided at a position near the proximal end of said balloon on the distal end portion made of optically transparent material.

8. An instrument according to claim 7, wherein said marking si disposed on said distal end portion so that when the marking is aligned with the verumontanum of the prostate as seen through the optical viewing means nd through said distal end portion, the balloon is correctly located relative to the prostatic urethra so that the balloon can be inflated so as to dilate the prostatic urethra without damaging the external sphincter at the apex of the prostate.

9. An instrument according to claim 7, wherein said marking id disposed ion the distal end portion so that when the marking is aligned with the apex of the prostate as seen through the optical viewing means and through the distal end portion, the ballon is correctly located relative to the prostatic urethra so that the balloon can be inflated so as to dilate the prostatic urethra without damaging the external sphincter at the apex of the prostate.

10. An instrument according to claim 7, wherein said marking is disposed on the distal end portion so that when the marking is aligned with the external sphincter of the prostate as seen through the optical viewing means and through the distal end portion, the balloon is correctly located relative to the prostatic urethra so that the balloon can be inflated so as to dilate the prostatic urethra without damaging the external sphincter at the apex of the prostate.

11. An instrument according of claim 6, wherein said balloon is approximately 30 mm in diameter along its length when inflated, and between about 5 and 6 cm in length.

12. An instrument according to claim 6, wherein said means for viewing said marking includes an optic of a commercially available cystoscope.

* * * * *

UNITED STATES PATENT AND TRADEMARK OFFICE
CERTIFICATE OF CORRECTION

PATENT NO. : 5,209,725

DATED : May 11, 1993

INVENTOR(S) : Robert A. Roth

It is certified that error appears in the above-identified patent and that said Letters Patent is hereby corrected as shown below:

```
Claim 1, column 10, line 35, delete "ctheter" and insert -- catheter --;
Claim 1, column 10, line 48, delete "ad" and insert -- and --;
Claim 1, column 10, line 59, delete "sad" and insert -- said --;

Claim 5, column 11, line 6, delete "mean" and insert -- means --;

Claim 8, column 12, line 4, delete "si" and insert -- is --;
Claim 8, column 12, line 7, delete "nd" and insert -- and --;
Claim 9, column 12, line 13, delete "id" and insert -- is --;
Claim 9, column 12, line 13, delete "ion" and insert -- on --;
Claim 9, column 12, line 16, delete "ballon" and insert -- balloon --;
Claim 11, column 12, line 30, delete "of" and insert -- to --.
```

Signed and Sealed this

Fifteenth Day of February, 1994

*Attest:*

BRUCE LEHMAN

*Attesting Officer*   *Commissioner of Patents and Trademarks*